United States Patent
Wein

(10) Patent No.: US 11,124,216 B1
(45) Date of Patent: Sep. 21, 2021

(54) MULTI-FUNCTIONAL STROLLER

(71) Applicant: Michael Wein, Houston, TX (US)

(72) Inventor: Michael Wein, Houston, TX (US)

(*) Notice: Subject to any disclaimer, the term of this patent is extended or adjusted under 35 U.S.C. 154(b) by 438 days.

(21) Appl. No.: 15/651,321

(22) Filed: Jul. 17, 2017

Related U.S. Application Data

(60) Provisional application No. 62/363,073, filed on Jul. 15, 2016.

(51) Int. Cl.
| | |
|---|---|
| B62B 9/08 | (2006.01) |
| B62B 5/04 | (2006.01) |
| B62B 7/00 | (2006.01) |
| B62B 7/04 | (2006.01) |
| B62B 5/00 | (2006.01) |
| A61B 5/024 | (2006.01) |
| B62B 9/06 | (2006.01) |

(52) U.S. Cl.
CPC ........ B62B 5/0404 (2013.01); A61B 5/02438 (2013.01); B62B 5/004 (2013.01); B62B 5/0069 (2013.01); B62B 7/006 (2013.01); B62B 7/04 (2013.01); B62B 9/08 (2013.01); *B62B 9/06* (2013.01)

(58) Field of Classification Search
CPC ..... B62B 5/0404; B62B 5/004; B62B 5/0069; B62B 7/006; B62B 7/04; B62B 9/08; A61B 5/02438
USPC .......................................................... 701/22
See application file for complete search history.

(56) References Cited

U.S. PATENT DOCUMENTS

| | | | | |
|---|---|---|---|---|
| 8,193,650 | B2* | 6/2012 | Thorne ................... | B62B 7/002 290/1 R |
| 8,376,374 | B2* | 2/2013 | Zhong ................... | B60B 33/026 280/47.38 |
| 8,398,096 | B2* | 3/2013 | Gower .................. | B62B 5/0438 280/47.18 |
| 8,448,976 | B2* | 5/2013 | Funakura .................. | B62B 7/08 280/642 |
| 8,469,861 | B1* | 6/2013 | McFee ............... | A63B 21/0059 482/5 |
| 8,585,076 | B2* | 11/2013 | Thorne ................... | B62B 7/068 280/650 |
| 9,108,658 | B2* | 8/2015 | Spencer .................. | B62B 9/087 |
| 9,254,858 | B2* | 2/2016 | Shellenberger ......... | B62B 9/087 |
| 10,414,207 | B2* | 9/2019 | Lai ...................... | B60B 33/0092 |
| 10,584,755 | B2* | 3/2020 | Peng ........................ | B62B 9/087 |
| 2007/0051566 | A1* | 3/2007 | Marlow .................... | B62B 5/04 188/20 |
| 2013/0341934 | A1* | 12/2013 | Kawanishi ............. | B61D 43/00 290/1 A |

(Continued)

FOREIGN PATENT DOCUMENTS

GB 2455529 A * 6/2009 ............... B62B 5/04

*Primary Examiner* — Peter D Nolan
*Assistant Examiner* — Wae L Louie
(74) *Attorney, Agent, or Firm* — Rao DeBoer Osterrieder, PLLC; Dileep P. Rao

(57) ABSTRACT

A multi-functional stroller comprising an incline detection system, and a braking system. The multi-functional stroller can detect when rolling uncontrolled, or when a user is not grasping the multi-functional stroller and engage the braking system to keep stroller occupant in safety. In embodiments, the multi-functional stroller can have motorized wheel hubs to aid in navigating stairs or uneven terrain.

19 Claims, 3 Drawing Sheets

(56) References Cited

U.S. PATENT DOCUMENTS

| | | | |
|---|---|---|---|
| 2014/0092612 A1* | 4/2014 | Freiser | B60Q 1/2657 |
| | | | 362/473 |
| 2015/0075575 A1* | 3/2015 | Karlovich | A61G 5/128 |
| | | | 135/66 |
| 2015/0198440 A1* | 7/2015 | Pearlman | G01S 17/86 |
| | | | 356/4.01 |
| 2015/0297439 A1* | 10/2015 | Karlovich | A61H 3/008 |
| | | | 280/650 |
| 2016/0014252 A1* | 1/2016 | Biderman | B60L 50/52 |
| | | | 455/420 |
| 2016/0023675 A1* | 1/2016 | Hannah | G05D 1/0011 |
| | | | 701/2 |
| 2016/0075175 A1* | 3/2016 | Biderman | B60W 50/085 |
| | | | 301/6.5 |
| 2016/0075177 A1* | 3/2016 | Biderman | H04M 1/72412 |
| | | | 301/6.5 |
| 2016/0075226 A1* | 3/2016 | Biderman | B60L 15/025 |
| | | | 301/6.5 |
| 2016/0082772 A1* | 3/2016 | Biderman | B60Q 9/00 |
| | | | 301/6.5 |
| 2016/0164371 A1* | 6/2016 | Rodger | B60T 1/005 |
| | | | 310/90.5 |
| 2016/0243927 A1* | 8/2016 | Biderman | B60L 58/21 |
| 2018/0056985 A1* | 3/2018 | Coulter | B60K 17/043 |
| 2019/0046373 A1* | 2/2019 | Coulter | A61G 5/063 |

* cited by examiner

MULTI-FUNCTIONAL STROLLER

CROSS REFERENCE TO RELATED APPLICATIONS

The present application claims priority and the benefit of U.S. Provisional Patent Application Ser. No. 62/363,073 filed on Jul. 15, 2016, titled "Stroller". This reference is incorporated herein in its entirety.

FIELD

The present disclosure generally relates to a multi-functional stroller apparatus for transporting a human.

BACKGROUND

There is often a need for transporting another human being in a wheeled device. Whether it is an adult that is bedridden or wheelchair bound, or a child or infant in a stroller.

Due to terrain or other structures needing to be navigated, the various devices currently in use have drawbacks or deficiencies that present dangers to the human being transported.

For example, use of a stroller for a child on a hill can be dangerous if the user loses their grip on the stroller. The stroller can roll into traffic or other nearby obstructions. This could result in injury to the child and/or the user attempting to recover control of the stroller.

Further, navigating hilly or rough terrain, as well as climbing stairs is difficult and unwieldy with currently available apparatuses.

A need exists, therefore for a multi-functional stroller which can automatically brake when uncontrolled and aid in navigating uneven terrain.

The present disclosure meets these needs.

BRIEF DESCRIPTION OF THE DRAWINGS

The detailed description will be better understood in conjunction with the accompanying drawings as follows.

Figure 1:
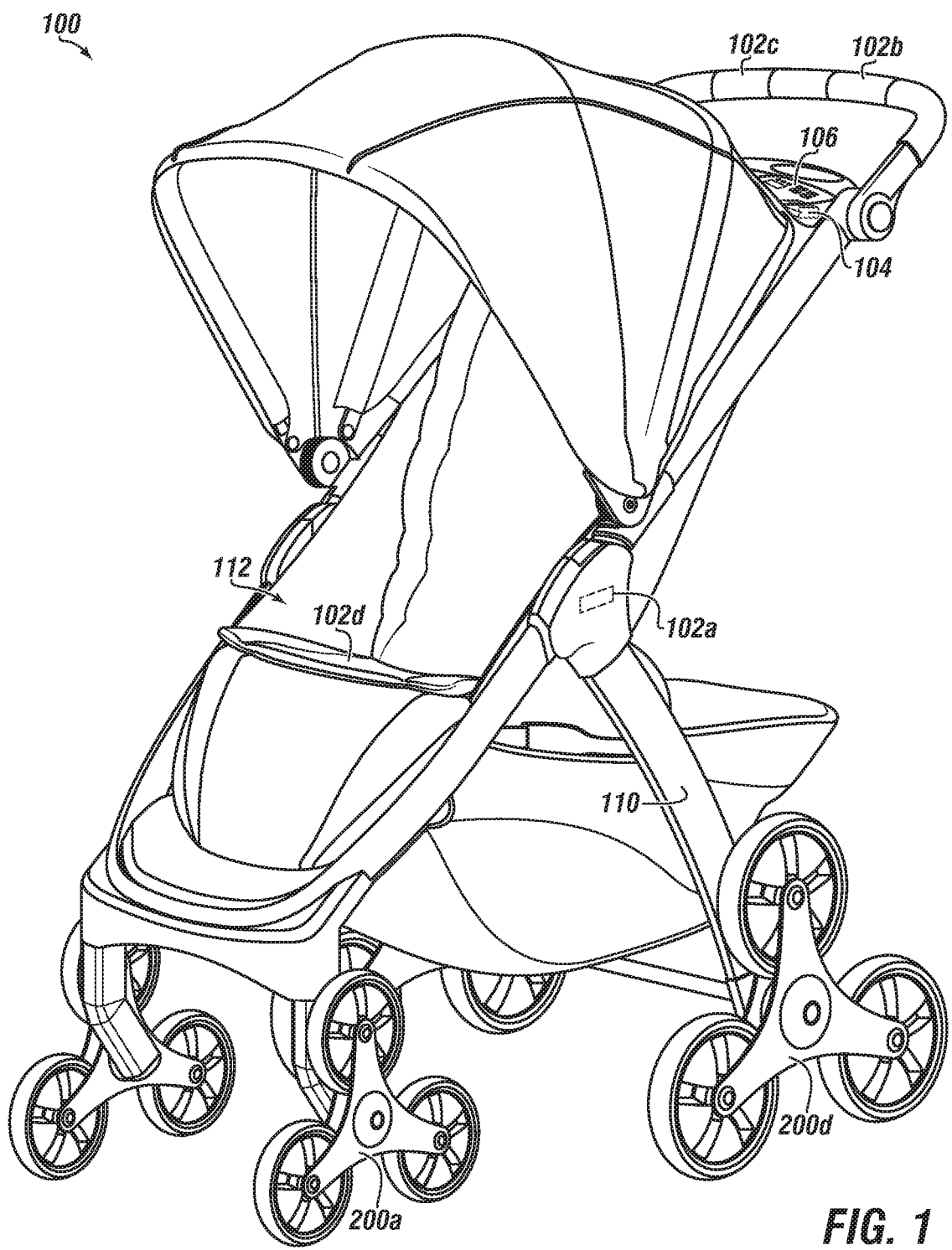
FIG. 1 depicts a multi-functional stroller according to one or more embodiments.

The embodiments of the present disclosure are detailed below with reference to the listed Figures.

DETAILED DESCRIPTION OF THE EMBODIMENTS

Before explaining the present invention in detail, it is to be understood that the invention is not limited to the specifics of particular embodiments as described and that it can be practiced, constructed, or carried out in various ways.

While embodiments of the disclosure have been shown and described, modifications thereof can be made by one skilled in the art without departing from the spirit and teachings of the disclosure. The embodiments described herein are exemplary only, and are not intended to be limiting.

Specific structural and functional details disclosed herein are not to be interpreted as limiting, but merely as a basis of the claims and as a representative basis for teaching persons having ordinary skill in the art to variously employ the present invention. Many variations and modifications of embodiments disclosed herein are possible and are within the scope of the present disclosure.

Where numerical ranges or limitations are expressly stated, such express ranges or limitations should be understood to include iterative ranges or limitations of like magnitude falling within the expressly stated ranges or limitations.

The use of the word "a" or "an" when used in conjunction with the term "comprising" in the claims and/or the specification may mean "one," but it is also consistent with the meaning of "one or more," "at least one," and "one or more than one."

The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description herein, but is only limited by the claims which follow, encompassing all equivalents of the subject matter of the claims. Each and every claim is hereby incorporated into the specification as an embodiment of the present disclosure. Thus, the claims are a further description and are an addition to the embodiments of the present disclosure.

The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

The embodiments of the present disclosure generally relate to a multi-functional stroller apparatus for transporting a human.

It should be noted that the term stroller is intended to encompass wheeled apparatuses for the purpose of transporting a human. Exemplary devices include, but are not limited to: strollers, prams, wheelchairs, hospital beds, and the like.

The multi-functional stroller can have a frame, a seating location for a person or a prone position location for a person, a handle for pushing or pulling, an incline detection system comprising a level sensor, a wheel speed sensor, or both the level sensor and the wheel speed sensor, and a brake.

The frame can comprise a structure to support the seating location for a person or the prone position location for a person. In embodiments, the seating location for a person or the prone position location for a person is detachable from the frame. The frame can also provide a location to attach the wheels and any ancillary devices as discussed below.

Persons having ordinary skill in the art are aware of various types of seats and attachments for transporting humans in a prone position. Any such variations can be utilized for the purposes of this disclosure.

In embodiments, the seating location can be detached from the frame and used as a car seat for infants or toddlers. Also in embodiments, the seating location for a person or the prone position location for a person can comprise a sensor for detecting a heart rate.

A handle for pushing or pulling the multi-functional stroller can be attached to the frame. In embodiments, the handle can also comprise one or more sensors for detecting a heart rate of the user, or to detect whether the user is grasping the handle. This can be done by various means as known to persons having ordinary skill in the art, such as temperature sensors, pressure sensors, sensors to detect electrical conductivity, heart rate sensors, and the like.

The multi-functional stroller can have an incline detection system. The incline detection system can have a level sensor, a wheel speed sensor, or both the level sensor and the wheel speed sensor.

The level sensor can detect the orientation angle of the multi-functional stroller. When an angle which is not substantially horizontal is detected, the level sensor can electronically transmit this information to a control system.

The wheel speed sensor can determine the speed of a wheel of the multi-functional stroller and transmit this information electronically to the control system. In alternate embodiments, a global positioning system (GPS) sensor can be utilized to transmit the position of the multi-functional stroller to the control system to calculate the speed of the multi-functional stroller.

Various other sensors can be in communication with the control system. Exemplary sensors include, but are not limited to: a sensor for measuring a heart rate, a sensor for detecting whether a user is grasping the handle, a sensor for detecting a distance from a user, and the like.

In embodiments, a sensor for measuring a heart rate can be installed in the seating location for a person or the prone position location for a person to provide a health indicator of the person being transported.

In embodiments, a sensor can be placed upon the handle to detect whether a user is grasping the handle. Various sensors well known to persons having ordinary skill in the art can be employed for this purpose. Exemplary sensors include, but are not limited to: pressure sensors, conductivity or resistivity sensors, temperature sensors, light sensors, photoelectric cells, and the like.

In embodiments, the multi-functional stroller can have a sensor for detecting the distance from a user. This sensor can be in electronic communication with a personal computing device of the user, such as a smartphone, tablet computer, or a laptop computer. In embodiments, the sensor can measure distance using laser, radar, sonar, or other methods known to persons having ordinary skill in the art.

The multi-functional stroller can have a brake in mechanical communication with one or more wheels. The brake can be any means of applying friction to one or more wheels of the multi-functional stroller. The brake can have a friction component and an actuator for displacing the friction component to make contact with one or more wheels of the multi-functional stroller. For example, the brake can be an inflatable bladder which can be inflated to apply friction to one or more wheels of the multi-functional stroller.

Various braking mechanisms can be employed. Exemplary brakes include disc brakes, drum brakes, the use of a bladder, applying one or more frictional "shoes" to each wheel, electromagnetic brakes when a dynamo or motor in communication with the wheel, and the like.

The multi-functional stroller can have a control system for engaging the brake. The control system can comprise a non-volatile data storage medium and a processor. In embodiments, the control system can be remote to the multi-functional stroller, such as an application on a personal computing device. Alternatively, the control system can be located on the multi-functional stroller.

In embodiments, the multi-functional stroller can have a dynamo in mechanical communication with a wheel of the stroller, and a battery in electronic communication with the dynamo. The battery can be that of a personal computing device attached to the multi-functional stroller, or a separate battery located on the multi-functional stroller. The dynamo can charge the battery when the wheels are in motion.

In embodiments, the multi-functional stroller can have a plurality of wheel hubs, wherein each wheel hub comprises a plurality of wheels. In embodiments, the multi-functional stroller can have at least one motor in mechanical communication with at least one wheel hub of the plurality of wheel hubs.

The multi-functional stroller can have a control system for operating the at least one motor to allow for assisted stair climbing, or navigation of irregular terrain.

The control system can comprise computer instructions on a non-volatile data storage medium which, when executed, instruct a processor to determine if the multi-functional stroller should be braked, and actuate the brake to engage one or more wheels if the multi-functional stroller should be braked.

The control system can comprise computer instructions on a non-volatile data storage medium which, when executed, instruct a processor to determine whether a user is grasping the handle, and actuate the brake to engage one or more wheels if the user is not grasping the handle.

The control system can comprise computer instructions on a non-volatile data storage medium which, when executed, instruct a processor to determine whether the multi-functional stroller exceeds a predetermined speed, and actuate the brake to engage one or more wheels if the predetermined speed is exceeded.

The control system can comprise computer instructions on a non-volatile data storage medium which, when executed, instruct a processor to determine whether the multi-functional stroller exceeds a predetermined angle of inclination, and actuate the brake to engage one or more wheels if the predetermined angle of inclination is exceeded.

Various decision-making logic can be employed by persons having ordinary skill in the art based upon the application. For example, the determination of when to brake for a children's stroller will be considerably variant from the determination of when to brake a hospital bed. The control system can be adapted to a specific scenario to determine when to brake the multi-functional stroller.

Accordingly, various sensors can be employed in electronic communication with the control system. In embodiments, the control system can be manually overridden by the user.

Turning now to the Figures, FIG. 1 depicts a multi-functional stroller according to one or more embodiments.

The multi-functional stroller 100 can have a frame 110 and a seating location for a person 112. Alternate embodiments can include a prone position location for a person. The embodiment shown comprises a control system 106 and a battery 104.

In embodiments seating location for a person 112 can be removable and/or also function as a car seat.

Various sensors 102*a*-102*d* in electronic communication with control system 106 are shown distributed on the multi-functional stroller 100. Sensor 102*a* can be for providing information about the multi-functional stroller 100. Exemplary sensors placed upon the frame can include tilt or attitude sensors, a level sensor, accelerometers, speed sensors, GPS sensors, altimeters, and the like.

Sensors 102*b* and 102*c* are shown placed upon the handle of the multi-functional stroller, and can be for providing information about a user. Exemplary sensors placed upon the handle can include heartbeat sensors, pressure transducers, current sensors, resistance sensors, and the like. Sensors 102*b* and 102*c* can be used to determine whether a user has a grip on the multi-functional stroller.

Sensor 102*d* can be for providing information about the passenger of the multi-functional stroller 100. Various sensors can be utilized based upon the desired information as known to persons having ordinary skill in the art.

The multi-functional stroller 100 can also have a wheel hub 200 with a plurality of wheels.

Figure 2A:
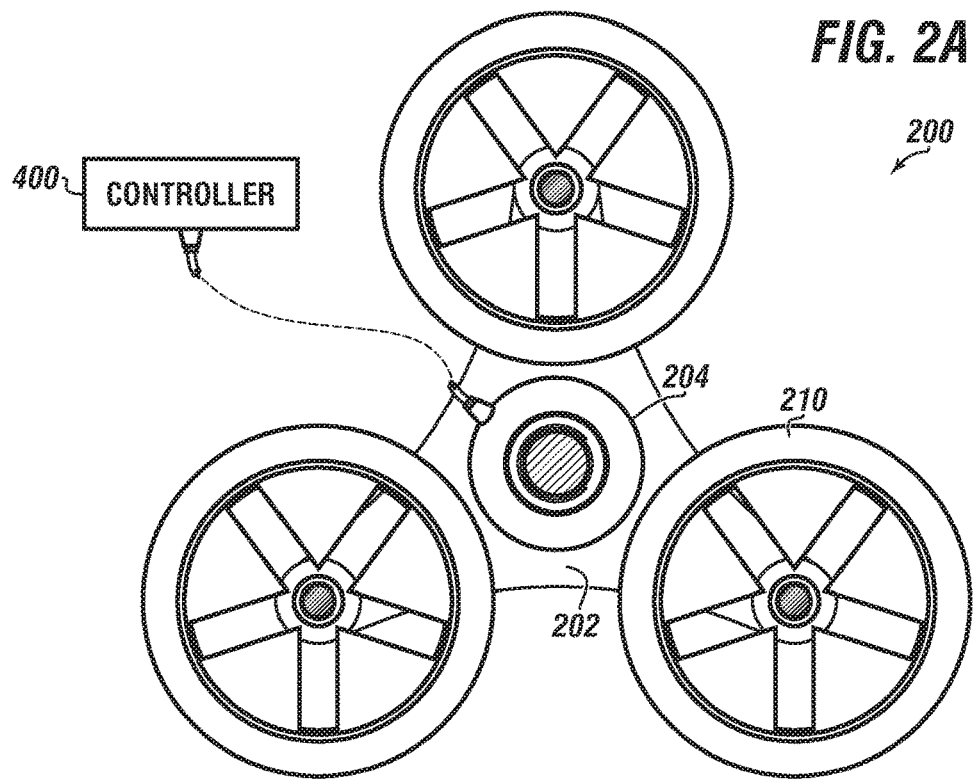
FIG. 2A depicts a wheel hub with a plurality of wheels with a brake in a disengaged position according to one or more embodiments.
Figure 2B:
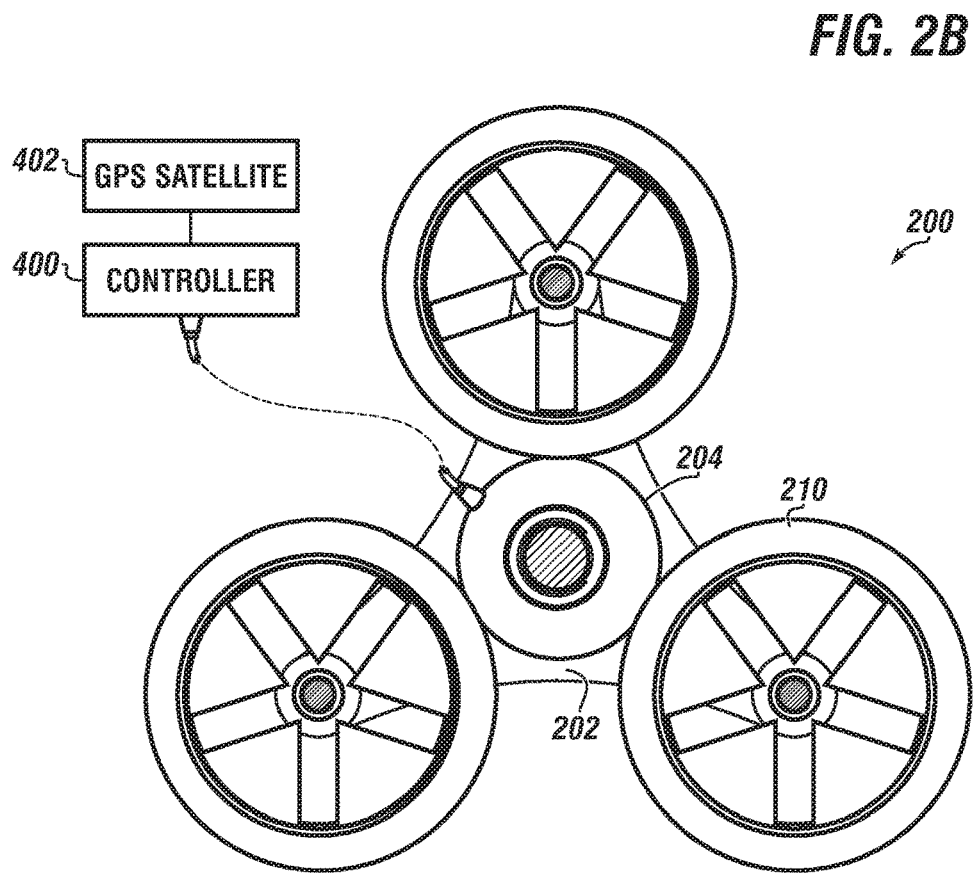
FIG. 2B depicts a wheel hub with a plurality of wheels with a brake in an engaged position according to one or more embodiments.

FIG. 2A depicts a wheel hub with a plurality of wheels with a brake in a disengaged position according to one or more embodiments. FIG. 2B depicts a wheel hub with a plurality of wheels with a brake in an engaged position according to one or more embodiments.

The wheel hub 200 can have a plurality of wheels 210 and a brake 204. A hub frame 202 can secure the various elements in the desired orientation and relative positions. In the embodiment shown, the brake 204 is in electronic communication with a controller 400. In embodiments, the controller 400 can be in electronic communication with a GPS satellite to determine position of the multi-functional stroller. In embodiments, the controller 400 can be in electronic communication with various other sensors as discussed above.

Figure 3:
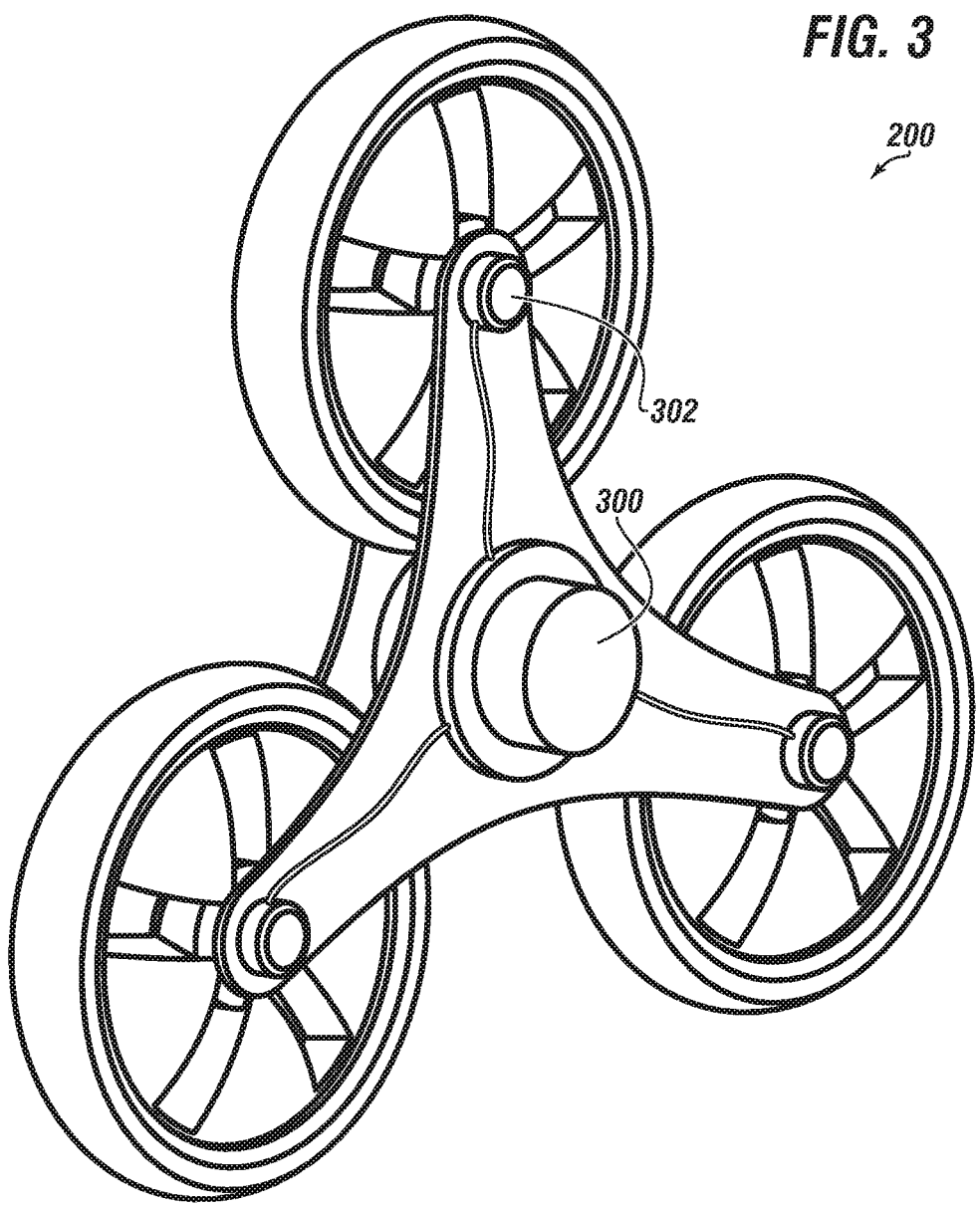
FIG. 3 depicts a perspective view of a wheel hub with a motor and dynamos on communication with the wheels according to one or more embodiments.

FIG. 3 depicts a perspective view of a wheel hub with a motor and dynamos on communication with the wheels according to one or more embodiments.

The wheel hub 200 can have a motor 300 which is configured to rotate the wheel hub when assisted motion of the multi-functional stroller is desired. In embodiments, each wheel can be in mechanical communication with a dynamo 302 for generating electricity with the motion of the wheel. The energy created by the dynamo 302 can be used to charge a battery.

Figure 4:
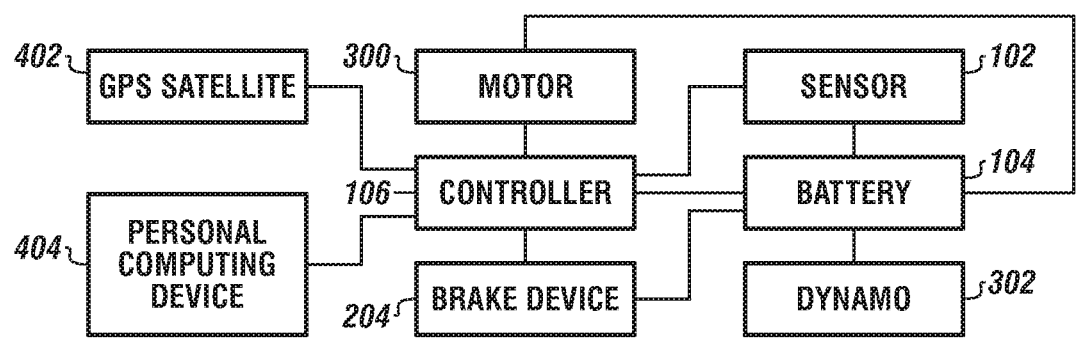
FIG. 4 depicts a schematic diagram of various components of the multi-functional stroller.

FIG. 4 depicts a schematic diagram of various components of the multi-functional stroller.

While the present disclosure emphasizes the embodiments, it should be understood that within the scope of the appended claims, the invention might be practiced other than as specifically described herein.

What is claimed is:

1. A multi-functional stroller comprising:
   a a frame;
   b a seating location for a person or a prone position location for a person;
   c a handle for pushing or pulling;
   d an incline detection system comprising a level sensor, a wheel speed sensor, or both the level sensor and the wheel speed sensor;
   e a brake; and
   f a control system in electronic communication with the incline detection system for engaging the brake when a specified incline or a specified wheel speed is exceeded and the multi-functional stroller is moving down the specified incline, and further wherein the incline detection system will selectively not engage the brake when the multi-functional stroller is moving up the specified incline.

2. The multi-functional stroller of claim 1, wherein the seating location for a person or the prone position location for a person is detachable from the frame.

3. The multi-functional stroller of claim 1, wherein the seating location, if used, is usable as a car seat for an infant or a toddler.

4. The multi-functional stroller of claim 1, further comprising a dynamo in mechanical communication with a wheel of the multi-functional stroller, and a battery in electronic communication with the dynamo.

5. The multi-functional stroller of claim 1, further comprising a sensor for detecting a position from a global positioning system.

6. The multi-functional stroller of claim 1, further comprising a sensor for measuring a heart rate.

7. The multi-functional stroller of claim 1, further comprising a sensor for measuring pressure.

8. The multi-functional stroller of claim 1, further comprising a sensor for detecting whether a user is grasping the handle.

9. The multi-functional stroller of claim 1, further comprising a sensor for detecting a distance from a user.

10. The multi-functional stroller of claim 1, further comprising a sensor for detecting a distance from a personal computing device.

11. The multi-functional stroller of claim 1, further comprising a plurality of wheel hubs, wherein each wheel hub comprises a plurality of wheels.

12. The multi-functional stroller of claim 11, further comprising at least one dynamo and a battery, wherein at least one wheel of the plurality of wheels is in mechanical communication with the at least one dynamo, and the at least one dynamo is in electronic communication with the battery.

13. The multi-functional stroller of claim 11, further comprising at least one motor in mechanical communication with at least one wheel hub of the plurality of wheel hubs.

14. The multi-functional stroller of claim 13, further comprising a control system in electronic communication the at least one motor.

15. The multi-functional stroller of claim 14, wherein the control system is configured to be selectively engaged by a user to rotate the at least one wheel hub of the plurality of wheel hubs.

16. The multi-functional stroller of claim 1, wherein the control system comprises computer instructions on a non-volatile data storage medium which, when executed, instruct a processor to determine if the multi-functional stroller should be braked, and actuate the brake to engage one or more wheels if the multi-functional stroller should be braked.

17. The multi-functional stroller of claim 1, wherein the control system comprises computer instructions on a non-volatile data storage medium which, when executed, instruct a processor to determine whether a user is grasping the handle, and actuate the brake to engage one or more wheels.

18. The multi-functional stroller of claim 1, wherein the control system comprises computer instructions on a non-volatile data storage medium which, when executed, instruct a processor to determine whether the multi-functional stroller exceeds a predetermined speed, and actuate the brake to engage one or more wheels.

19. The multi-functional stroller of claim 1, wherein the control system comprises computer instructions on a non-volatile data storage medium which, when executed, instruct a processor to determine whether the multi-functional stroller exceeds a predetermined angle of inclination, and actuate the brake to engage one or more wheels.

* * * * *